(12) United States Patent
Yamaguchi et al.

(10) Patent No.: US 7,005,661 B2
(45) Date of Patent: Feb. 28, 2006

(54) OPTICAL OBJECT IDENTIFICATION APPARATUS, AND PRINTING APPARATUS AND OBJECT CLASSIFICATION APPARATUS USING SAME

(75) Inventors: Akifumi Yamaguchi, Kashiba (JP); Hisakazu Sugiyama, Takarazuka (JP)

(73) Assignee: Sharp Kabushiki Kaisha, Osaka (JP)

( * ) Notice: Subject to any disclaimer, the term of this patent is extended or adjusted under 35 U.S.C. 154(b) by 160 days.

(21) Appl. No.: 10/726,068

(22) Filed: Dec. 3, 2003

(65) Prior Publication Data
US 2004/0129901 A1    Jul. 8, 2004

(30) Foreign Application Priority Data
Dec. 3, 2002    (JP) ............................ P2002-350900

(51) Int. Cl.
*G01N 21/86* (2006.01)
(52) U.S. Cl. .................................. 250/559.16; 250/225
(58) Field of Classification Search ............ 250/559.4, 250/559.41, 559.44, 559.22; 356/445, 446
See application file for complete search history.

(56) References Cited
U.S. PATENT DOCUMENTS 5,162,660 A * 11/1992 Popil .................... 250/559.01
5,736,735 A * 4/1998 Hagiwara ................ 250/225
6,291,829 B1 * 9/2001 Allen .................... 250/559.07

FOREIGN PATENT DOCUMENTS

| JP | 10-198174 | 7/1998 |
|---|---|---|
| JP | 2000-301805 | 10/2000 |
| JP | 2001-88275 | 4/2001 |

* cited by examiner

*Primary Examiner*—David Porta
*Assistant Examiner*—Tony Ko
(74) *Attorney, Agent, or Firm*—Nixon & Vanderhye P.C.

(57) ABSTRACT

An optical object identification apparatus has a light emitting-side optical system (23), a light receiving-side optical system (26), and a signal processing section (29). The light emitting-side optical system (23) irradiates light from a light emitting device (21) via an objective lens (22) to a moving target object (27) such as printing paper sheets. The light receiving-side optical system (26) receives reflected light from the target object by means of the light receiving device (25) via an objective lens (24), and outputs an output signal with a waveform corresponding to the surface projections and depressions of the target object (27). The signal processing section (29) executes signal processing on the output signal by at least one signal processing method to identify the target object.

29 Claims, 8 Drawing Sheets

US 7,005,661 B2

OPTICAL OBJECT IDENTIFICATION APPARATUS, AND PRINTING APPARATUS AND OBJECT CLASSIFICATION APPARATUS USING SAME

This application claims priority of JP Application No. 2002-350900 filed 3 Dec. 2002, the entire contents of which is incorporated herein by reference.

BACKGROUND OF THE INVENTION

The present invention relates to an optical object identification apparatus for detecting the type of objects without contact, and also relates to a printing apparatus and an object classification apparatus using the same.

Copying apparatuses and printing apparatuses that conduct recording processing while conveying recording media are being developed to achieve high function, high-speed processing and high resolution, and the recording media used thereby are of varied types including plain paper, glossy paper and OHP (Overhead Projector) sheets. When images are printed on such widely varying recording media by means of a printer (especially an ink jet printer) that is an image recording apparatus, it is necessary, for forming high-quality images, to execute recording control corresponding to the respective recording media because the infiltration rate and the dry time of an ink are different depending on the type of the recording media.

Conventionally, as methods for detecting the type of recording media including paper media such as printer paper, as well as resin films and sheets, there have been a mechanical detection method, a thermal detection method and an optical detection method. The mechanical detection method is for detecting the type of a recording medium by the displacement amount of a contact and the like when the recording medium is inserted into a conveyor portion. The thermal detection method is for detecting the type of a recording medium by placing a thermal element on the recording medium and detecting the thermal change of the recording medium or of the heating element itself.

In the optical detection method, a light emitting device and a light receiving device are provided, and a recording medium is irradiated with light from the light emitting device so that the type of the recording medium is detected by the amount of reflected light from the recording medium. For example, in "Paper Kind Detector and Image Forming Device Provided with the Same" disclosed in Japanese Patent Laid-Open Publication HEI No. 10-198174, as shown in FIG. 15, the type of a paper sheet 3 is detected by the change of an output from a light receiving device 2 based on the placement angles of two light emitting devices 1a, 1b and the light receiving device 2 with respect to the paper sheet 3. Further, in "Identification of Recording Medium in a Printer" disclosed in Japanese Patent Laid-Open Publication No. 2000-301805, and in its equivalent U.S. Pat. No. 6,291,829 B1, as shown in FIG. 16, light from a transmission illuminator 11 passes a recording medium 12, light with a grazing incidence from a grazing illuminator 13 irradiates the recording medium 12, and light from a vertical illuminator 14 vertically irradiates the recording medium 12 via an amplitude beam splitter 15. Then, a surface image of the recording medium 12 is obtained by a photodetector array 16 such as CCD (Charge Coupled Device) and C-MOS (Complementary Metal Oxide Semiconductor) devices, and the obtained image is subject to two-dimensional image processing to identify the type of the recording medium 12.

Further, there is a method for detecting the type of recording media, in which a detection liquid containing a specified pigment or a fluorescent material is infiltrated into a recording medium, and light in the wavelength range absorbed by the pigment or the fluorescent material is irradiated to a portion of the recording medium infiltrated with the detection liquid to determine the intensity of reflected light, or infrared radiation is irradiated to measure the infrared absorption spectrum of reflected light (see Japanese Patent Laid-Open Publication No. 2001-88275 for example).

However, the above-mentioned conventional methods for detecting the type of recording media suffer a following problem.

That is, in the case of the mechanical detection method and the thermal detection method, a contact and a heating element should be brought into contact with a recording medium, which may disturb the movement of the recording medium during conveyance, and may also cause the deformation of the recording medium. Moreover, detection failure due to the deterioration of a contact section caused by wear may occur.

Further, in the case of the aforementioned optical detection methods, the type of a recording medium is detected by the difference in the amount of reflected light from the recording medium, and therefore detection may not be possible if the difference in the amount of reflected light is small, causing considerable restraint of detectable types of recording media. Furthermore, attention needs to be paid to the adjustment of placement angles of the light emitting device and the light receiving device, which makes assemblage of the apparatus complicated.

Furthermore, in the case of the method in which an image sensor such as CCD and C-MOS devices is used in a light receiving section, image processing becomes complicated, and pursuing higher identification accuracy increases the number of elements to be identified, thereby making the processing more complicated as well as making the light receiving device expensive. In the case of the method in which a detection liquid is infiltrated into the recording medium at a portion to measure reflected light from that portion of the infiltrated medium, the recording medium is possibly given pigmentary change and fouling. In addition, this method requires a means for infiltrating the detection liquid, which causes growing in size of the apparatus, and measuring the infrared absorption spectrum complicates the configuration and signal processing of the light receiving portion.

SUMMARY OF THE INVENTION

Accordingly, an object of the present invention is to provide an optical object identification apparatus that allows easy identification of the various types of objects with use of reflected rays of light from target objects, and to provide a printing apparatus and an object classification apparatus using the same.

An optical object identification apparatus according to the present invention includes at least one light emitting-side optical system that includes a light emitting device and an objective lens, and that irradiates light from the light emitting device to a moving target object and forms a light spot on the target object; at least one light receiving-side optical system that includes a light receiving lens and a light receiving device, and that outputs an output signal having a waveform corresponding to surface projections and depressions of the target object when reflected light from the light spot enters the light receiving device; and a signal processing section that executes signal processing of the output signal outputted from the light receiving-side optical system.

According to the above constitution, based on the reflected light from the light spot on the moving target object, the light receiving device of the light receiving-side optical system outputs an output signal with a waveform corresponding to the surface projections and depressions of the target object. Therefore, executing signal processing on the output signal in the signal processing section makes it possible to obtain a processing result that allows identification of the type of the target object.

Thus, based on the output signal having the waveform corresponding to the surface projections and depressions of the target object, it becomes possible to identify a larger number of types of the objects with more accuracy than the conventional cases in which the types of the objects are identified based on the amount of reflected light from the target objects.

In one embodiment, a semiconductor laser is used as the light emitting device.

According to this embodiment, the light emitting device is a semiconductor laser, so that light from the light emitting device is condensed efficiently by means of the objective lens. Therefore, it becomes possible to obtain a necessary amount of reflected light for obtaining an output signal that allows identification of the type of the target object with more accuracy.

In one embodiment, the optical object identification apparatus includes a pair of the one light emitting-side optical system and the one light receiving-side optical system, and an optical axis of the light emitting-side optical system and an optical axis of the light receiving-side optical system are vertical to a light spot formation face on the target object.

According to this embodiment, even if a distance between the optical object identification apparatus and the target object is fluctuated due to vibration or the like of the target object, the light spot on the target object exists on the optical axis of the light receiving-side optical system. Therefore, the reflected light from the light spot precisely enters the light receiving-side optical system even if the distance between the optical object identification apparatus and the target object is fluctuated. Thus, the optical object identification apparatus that is less susceptible to fluctuation of the distance to the target object is provided.

In one embodiment, the optical object identification apparatus has one light emitting-side optical system and two light receiving-side optical systems, and an angle between an optical axis of one of the two light receiving-side optical systems and a light spot formation face of the target object is equal to an angle between an optical axis of the light emitting-side optical system and the light spot formation face of the target object.

According to this embodiment, a regularly reflected or specularly reflected light from the light spot on the target object enters the one of the two light receiving-side optical systems, whereas a diffuse-reflected light from the light spot enters the other light receiving-side optical system. Therefore, by comparing a processing result based on the regularly reflected light from the signal processing section and a processing result based on the diffuse-reflected light, it becomes possible to identify the type of the target object more accurately than the case in which identification is achieved only from the processing result based on the regularly reflected light.

In one embodiment, the light emitted from the light emitting device is polarized light whose direction of polarization is vertical to a plane of incidence.

In one embodiment, the light emitted from the light emitting device is polarized light whose direction of polarization is parallel to a plane of incidence.

According to these embodiments, if the light receiving-side optical system is enabled to receive two types of reflected light, i.e., polarized light whose direction of polarization is orthogonal to the direction of polarization of light from the light emitting device, and a natural light, it becomes possible to know the degree of deflection of the polarization direction of the light from the light emitting device at a point of the target object at the time of reflection (the degree is different depending on the type of the target object) based on the result of processing in the signal processing section. Therefore, by comparing the processing result based on the polarized light and the processing result based on the natural light, the type of the target object can be identified with more accuracy than the case in which identification is achieved only from the processing result based on the natural light.

In one embodiment, the light receiving-side optical system has two light receiving devices. And, the optical object identification apparatus further includes a beam splitter provided in the light receiving-side optical system for letting the reflected light from the light spot come incident to each of the two light receiving devices; and polarization means disposed immediately before one of the light receiving devices in the light receiving-side optical system for passing polarized light having a direction of polarization that is orthogonal to the direction of polarization of the light emitted from the light emitting device.

According to this embodiment, the light receiving-side optical system makes it possible to easily obtain two types of output signals based on two types of reflected light, i.e., polarized light whose direction of polarization is orthogonal to the direction of polarization of light from the light emitting device, and natural light.

In one embodiment, two light receiving regions are provided in the light receiving device. And the optical object identification apparatus includes a diffraction grating provided in the light receiving-side optical system and designed such that intensity of zero-order diffraction light is sufficiently smaller than intensity of ± first-order diffraction light; and polarization means disposed immediately before one of the light receiving regions in the light receiving device for passing polarized light having a direction of polarization that is orthogonal to the direction of polarization of the light emitted from the light emitting device. The ± first-order diffraction light from the diffraction grating enters the two right receiving regions.

According to this embodiment as well, the light receiving-side optical system makes it possible to easily obtain two types of output signals based on two types of reflected light, i.e., polarized light whose direction of polarization is orthogonal to the direction of polarization of light from the light emitting device, and natural light.

In one embodiment, the light receiving device in the light receiving-side optical system is disposed in a position closer to the light receiving lens than a location of an image of the light spot formed by the light receiving lens is. Polarization means is disposed immediately before a half region of a light receiving face in the light receiving device for passing polarized light having a direction of polarization that is orthogonal to the direction of polarization of the light emitted from the light emitting device, and an image of the light spot formed on the light receiving face of the light receiving device by the light receiving lens is formed in a boundary between a region of the light receiving face on which the polarization means is disposed and a region of the light receiving face on which the polarization means is not disposed.

According to this embodiment as well, the light receiving-side optical system makes it possible to easily obtain two types of output signals based on two types of reflected light, i.e., polarized light whose direction of polarization is orthogonal to the direction of polarization of light from the light emitting device, and natural light.

In one embodiment, the polarization means is provided by a polarization device formed on the light receiving device or on the light receiving region.

According to this embodiment, it becomes possible to form the polarization means and the light receiving device in one chip.

In one embodiment, the signal processing section executes signal processing on a section of specified length of time in the output signal by at least one signal processing method selected from the group consisting of:

a mean value calculating method of calculating a mean value of output values;

a mean amplitude value calculating method of obtaining differences between each of the output values and the mean value and doubling a mean value of absolute values of these differences;

a mean-amplitude/mean value calculating method of calculating the mean amplitude value divided by the mean value;

a frequency distribution calculating method of obtaining frequency distribution of the output values with a maximum value being set to 1;

a power spectral area ratio calculating method of obtaining spectral distribution by applying Fourier transform and obtaining an area ratio between different distribution ranges in the spectral distribution; and a filter passing method of calculating at least one of the mean value, the mean amplitude value, and the mean amplitude divided by the mean value after passing the output signal through a filter circuit.

According to this embodiment, the type of the target object can be identified more accurately than the case in which the type is identified simply based on the amount of reflected light from the target object.

In one embodiment, the signal processing section executes signal processing by at least two of the mean value calculating method, the mean amplitude value calculating method, the mean-amplitude/mean value calculating method, the frequency distribution calculating method, the power spectral area ratio calculating method, and the filter passing method, and calculates a ratio between processing results obtained by these two signal processing methods.

According to this embodiment, the type of the target object can be identified more accurately than the case in which identification is made only from the processing result by one signal processing method.

In one embodiment, the signal processing section executes signal processing on respective output signals from the two light receiving-side optical systems by at least any one of the mean value calculating method, the mean amplitude value calculating method, the mean-amplitude/mean value calculating method, the frequency distribution calculating method, the power spectral area ratio calculating method, and the filter passing method, and calculates a ratio between processing results for these two light receiving-side optical systems.

According to this embodiment, the type of the target object can be identified more accurately than the case in which identification is made only from the processing result for only one light receiving-side optical system.

In one embodiment, the signal processing section executes signal processing on two types of output signals that are respectively based on light that has passed the polarization means and light that has not passed the polarization means, by at least any one of the mean value calculating method, the mean amplitude value calculating method, the mean-amplitude/mean value calculating method, the frequency distribution calculating method, the power spectral area ratio calculating method, and the filter passing method, and calculates a ratio between processing results of these two types of output signals.

According to this embodiment, the type of the target object can be identified more accurately than the case in which identification is made only from the processing result based on the light that has not passed the polarization means.

In one embodiment, the optical object identification apparatus includes another light receiving-side optical system also having the polarization means. The signal processing section executes signal processing on two types of output signals that are respectively based on light that has passed the polarization means and light that has not passed the polarization means, for each of the two light receiving-side optical systems, by at least any one of the mean value calculating method, the mean amplitude value calculating method, the mean-amplitude/mean value calculating method, the frequency distribution calculating method, the power spectral area ratio calculating method, and the filter passing method, and calculates a ratio between processing results of the output signals of the two light receiving-side optical systems based on the light that has passed the respective polarization means, and a ratio between processing results of the output signals of the two light receiving-side optical systems based on the light that has not passed the polarization means.

According to this embodiment, the type of the target object can be identified with much further accuracy.

In one embodiment, the signal processing section executes signal processing on a plurality of different sections in the output signal obtained by movement of the target object, by at least any one of the mean value calculating method, the mean amplitude value calculating method, the mean-amplitude/mean value calculating method, the frequency distribution calculating method, the power spectral area ratio calculating method, and the filter passing method, and calculates a mean value of processing results of the plurality of the sections.

According to this embodiment, the type of the target object can be identified more accurately than the case in which identification is made only from the processing result of one section only.

A printing apparatus according to the present invention incorporates the above optical object identification apparatus.

According to the above constitution, the optical object identification apparatus incorporated in the printing apparatus is capable of obtaining a processing result that allows identification of the type of a target object, by executing signal processing of an output signal with a waveform corresponding to the surface projections and depressions of the target object. Therefore, types of paper sheets, films and the like, that are subject to printing, can be accurately identified. This makes it possible to optimize printing conditions and increase printing quality.

Further, an object classification apparatus according to the present invention incorporates the aforementioned optical object identification apparatus.

In the apparatus, the incorporated optical object identification apparatus is capable of obtaining a processing result that allows identification of the type of a target object, by executing signal processing of an output signal with a waveform corresponding to the surface projections and depressions of the target object. Therefore, types of objects can be accurately identified.

Other objects, features and advantages of the present invention will be apparent from the following description.

BRIEF DESCRIPTION OF THE DRAWINGS

The present invention will become more fully understood from the detailed description given hereinbelow and the accompanying drawings which are given by way of illustration only, and thus are not intended to limit the present invention, and wherein:

FIG. 8 is formed from a polarization device;

DETAILED DESCRIPTION OF THE PREFERRED EMBODIMENTS

Figure 1:
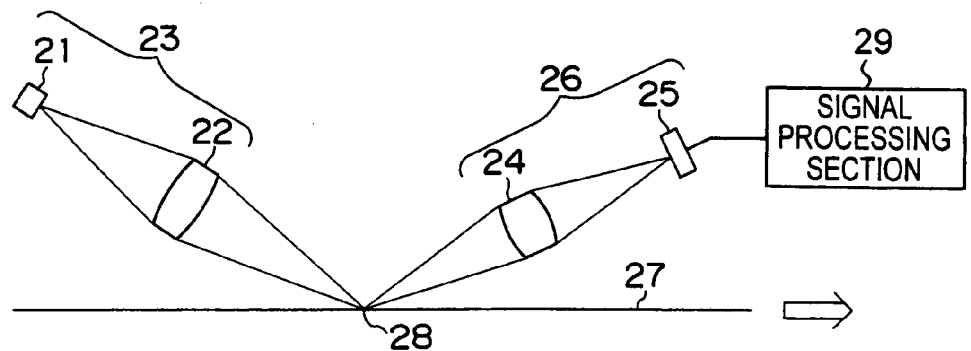
FIG. 1 is a schematic diagram showing optical systems in an optical object identification apparatus of the present invention.

The present invention will be described in detail below on the basis of the embodiments shown in the drawings.

(First Embodiment)

FIG. 1 is a schematic diagram showing an optical system in an optical object identification apparatus of the present embodiment. The optical object identification apparatus has at least one light emitting-side optical system 23 including a light emitting device (preferably a semiconductor laser) 21 and an objective lens 22, and at least one light receiving-side optical system 26 including a light receiving lens 24 and a light receiving device 25. By irradiating light emitted from the light emitting-side optical system 23 to a target object 27, a light spot 28 having a predetermined spot diameter (not more than 50 $\mu$m) is formed on the target object 27 moving in an arrow direction, so that reflected light from the light spot 28 enters the light receiving-side optical system 26.

Figure 2:
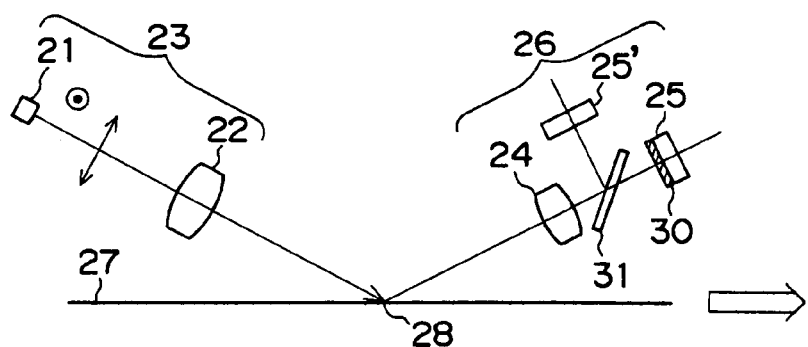
FIG. 2 is a detailed explanatory view showing a light emitting-side optical system and a light receiving-side optical system in FIG. 1.

Hereinbelow, detailed description will be given of the light emitting-side optical system 23 and the light receiving-side optical system 26. As shown in FIG. 2, in the light emitting-side optical system 23, the direction of polarization of the light emitted from the light emitting device 21 is set vertical (or parallel) to the plane of incidence. In the light receiving-side optical system 26, reflected light from the target object 27 is received in the state of being split into light polarized parallel (or vertical) to the plane of incidence and natural light. In this connection, in the light receiving-side optical system 26, two light receiving devices 25, 25' are provided such that their optical axes are orthogonal to each other, and a polarizer 30 is disposed on the front surface of one light receiving device 25 for passing the light polarized parallel (or vertical) to the plane of incidence. Nothing is disposed on the front surface of the other light receiving device 25'. Then, the light entering the light receiving-side optical system 26 is split by a beam splitter 31 and brought incident upon the respective light receiving devices 25, 25' (one is via the polarizing plate 30).

Figure 3A:
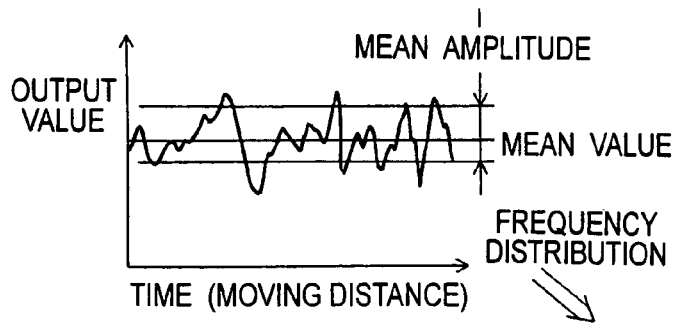
FIGS. 3A, 3B and 3C are explanatory views showing the waveform of an output signal from a he light receiving device shown in FIG. 1 and various signal processings by a signal processing section in FIG. 1.

In this stage, as the target object 27 moves, output signals from the light receiving devices 25, 25' show output waveforms corresponding to the surface state (surface projections and depressions) of the target object 27 as shown in FIG. 3A. Consequently, a signal processing section 29 executes signal processing of a section of specified length of time in the output signals, by which the type of the target object 27 can be identified more accurately than the case in which the type is identified based on the amount of reflected light from the target object in a conventional manner.

Figure 3B:
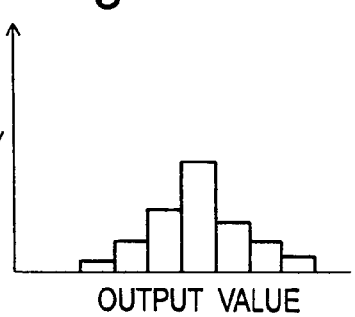
Figure 3C:
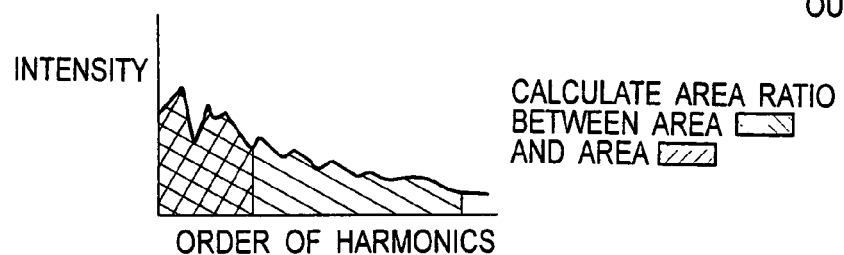

For processing the output signals in the above case, there is used any one of the following signal processing methods for calculating: a mean value of a specified length section in the output signals from the light receiving devices 25, 25'; a mean amplitude value; a mean amplitude value/mean value (that is, the mean amplitude value divided by the mean value); frequency distribution; a power spectral area ratio; and at least one of the mean value, the mean amplitude value, and the mean amplitude value/mean value of the waveforms after passing a filter circuit. Herein, the mean amplitude value is defined as a value calculated by obtaining differences between the individual output values of the output signals and their mean value and doubling a mean value of the absolute values of the thus obtained differences. The frequency distribution is defined as a frequency distribution of the output values with a maximum output value being set to "1" as shown in FIG. 3B. The power spectral area ratio is defined as an area ratio of a specified distribution range to another specified distribution range in a spectral distribution that is obtained by applying Fourier transform to the output signals as shown in FIG. 3C. It is noted that the above-stated signal processing methods are hereinafter respectively referred to as the "mean value calculating method", "mean amplitude value calculating method", "mean-amplitude/mean value calculating method", "frequency distribution calculating method", "power spectral area ratio calculating method", and "filter passing method".

Figure 4:
FIG. 4 is a view showing mean values of output signals in connection with plural types of target objects.

Now, if the output signal from the aforementioned one light receiving device 25 (or the light receiving device 25') only undergoes one of the signal processing methods, the type of the target object 27 may be identified, though there may be cases where all the types of the target objects 27 are not definitely identified. In the case of applying the "mean value calculating method" for example, the value varies depending on the types of the target objects 27 as shown in FIG. 4, and some types can be identified. However, definite identification is difficult to achieve when the difference among the mean values for respective types is small as seen between types A and C, and types D and E. Likewise, the success of identification of the target objects 27 depends on the types of the target objects also in the case of the aforementioned "mean amplitude value calculating method", "mean-amplitude/mean value calculating method", "frequency distribution calculating method", "power spectral area ratio calculating method", and "filter passing method".

In the present embodiment, however, the light receiving-side optical system 26 is provided with the light receiving device 25 incorporating the polarizing plate 30 and the light receiving device 25' without incorporating the polarizing plate. The direction of polarization of laser light is changed or deflected when the light is reflected on the target object 27, and the degree of this deflection varies depending on the type of the target object 27. Therefore, if any one of the aforementioned signal processing methods is executed on a detection signal from the light receiving device 25 incorporating the polarizing plate 30 and a detection signal from the light receiving device 25' without incorporating the polarizing plate, respectively, and these processing results are compared, then more definite identification of the type of the target object 27 may be achieved.

Accordingly, the signal processing section 29 executes at least one signal processing method selected from the group consisting of the "mean value calculating method", the "mean amplitude value calculating method", the "mean-amplitude/mean value calculating method", the "frequency distribution calculating method", the "power spectral area ratio calculating method", and the "filter passing method" on each of the detection signal from the light receiving device 25 and the detection signal from the light receiving device 25', and calculates a ratio between processing results of those detection signals.

Thus, polarization is utilized in the optical object identification apparatus in the present embodiment. This makes it possible to detect the degree of deflection of the polarization direction of laser light at a point of the target object 27 at the time of reflection to implement more definite identification of the type of the target object 27.

Although in the above description, the light entering the light receiving-side optical system 26 is brought incident upon two different light receiving devices 25, 25' by the beam splitter 31, the present invention is not limited thereto.

Figure 5:
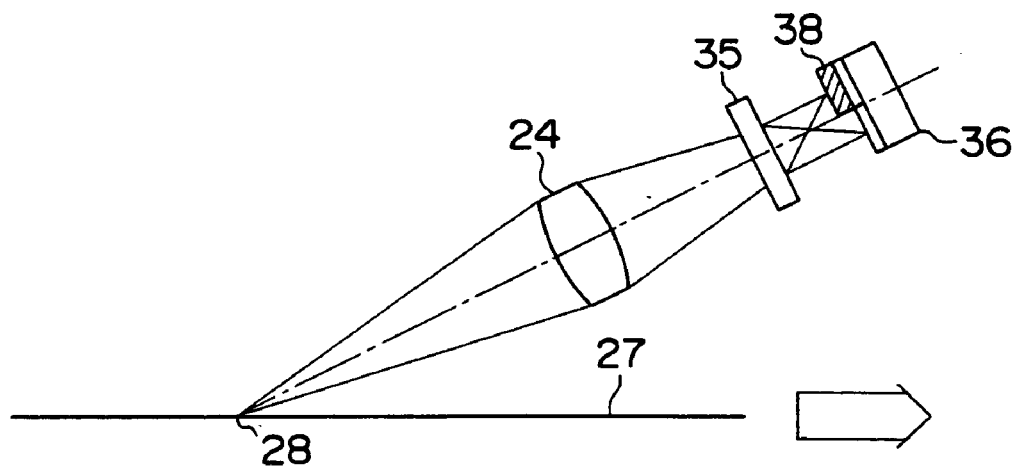
FIG. 5 is a detailed explanatory view showing a light receiving-side optical system different from that in FIG. 2.
Figure 6:
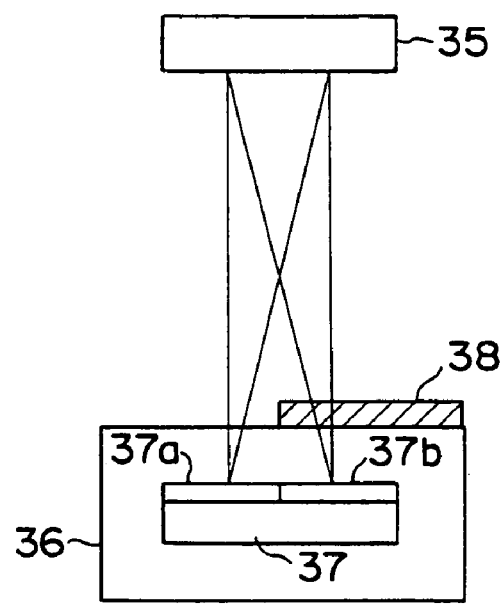
FIG. 6 is an explanatory view showing the specific constitution of a light receiving device in FIG. 5.

For example, as shown in FIG. 5 (in which the light emitting-side optical system 23 is omitted), a diffraction grating 35 for setting the intensity of zero-order diffraction light considerably smaller than the intensity of ± first-order diffraction light is disposed in the rear of the light receiving lens 24. Then, in the rear of the diffraction grating 35, a light receiving device 36 composed of a single chip 37 having two light receiving regions 37a, 37b is disposed as shown in FIG. 6. Then, in front of one light receiving region 37b in the light receiving device 36, a polarizing plate 38 for passing light polarized parallel (or vertical) to the plane of incidence my be disposed.

Figure 7:
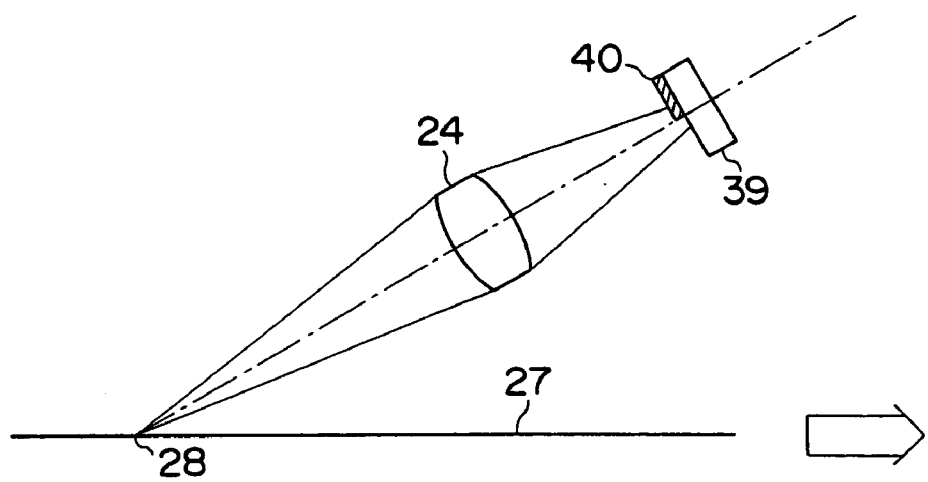
FIG. 7 is a detailed explanatory view showing a light receiving-side optical system different from those in FIG. 2 and FIG. 5.

Alternatively, as shown in FIG. 7 (in which the light emitting-side optical system 23 is omitted), a light receiving device 39 is disposed slightly before the position in which an image of the light spot 28 is formed by the light receiving lens 24 of the light receiving-side optical system (i.e., the position closer to the light receiving lens 24). Then, as shown in FIG. 8, a half region of the light receiving face of the light receiving device 39 is covered with a polarizing plate 40 that passes light polarized parallel (or vertical) to the plane of incidence, so that the reflected light from the light spot 28 on the target object 27 enter two light receiving regions (with one region via the polarizer 40).

Figure 8:
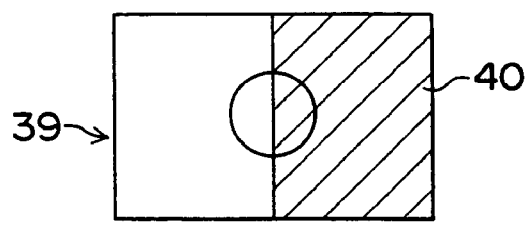
FIG. 8 is an explanatory view showing a light receiving device and a polarizing plate in FIG. 7.
Figure 9:
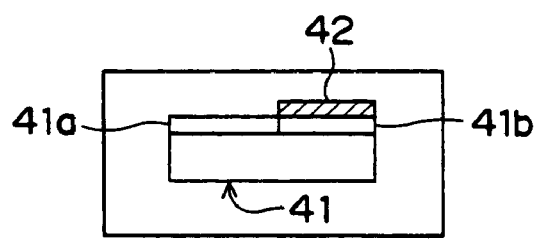
FIG. 9 is an explanatory view showing the case in which the polarizing plate in FIG. 6

It is noted that the polarizing plate 38 shown in FIG. 6 and the polarizing plate 40 shown in FIG. 8 may preferably be composed of a polarization device 42 formed on one 41b of two light receiving regions 41a, 41b of a light receiving chip 41, as shown in FIG. 9.

Also, in the above embodiment, the ratio between the signal processing results of the detection signal that has passed the polarizer and the detection signal that has not passed the polarizer is calculated, but the present invention is not limited thereto.

For example, in the constitution of FIG. 1 without use of the polarizer, the signal processing section 29 may execute any combination of the aforementioned signal processing methods: the "mean value calculating method", "mean amplitude value calculating method", "mean-amplitude/mean value calculating method", "frequency distribution calculating method", "power spectral area ratio calculating method", and "filter passing method", and calculate a ratio between thus obtained processing results. Thus, using some of the signal processing methods in combination also accomplish more definite identification of the type of the target object 27, and therefore if the types of the target objects 27 further increase, identification is still possible by combining a plurality of the signal processing methods. In such a case, the signal processing section 29 may execute a combination of a plurality of the signal processing methods in parallel by a plurality of signal processing means or in time series by a single signal processing means.

Alternatively, in the constitution of FIG. 1 without use of the polarizer, the signal processing section 29 may execute at least one of the aforementioned signal processing methods on a specified length section (specified length of time) of the output signal from the light receiving device 25 a plurality of times, and calculate a mean value of a plurality of the obtained processing results.

Alternatively, a plurality of pairs of the light receiving-side optical system and the signal processing section may be provided, and these light receiving-side optical systems may be given an identical photo-acceptance angle. Then, the different pairs may execute different signal processing methods and based on the thus obtained signal processing results, a discriminating means may determine the type of the target object 27. In such a case, it is possible to apply polarization to one light receiving-side optical system.

(Second Embodiment)

Figure 10:
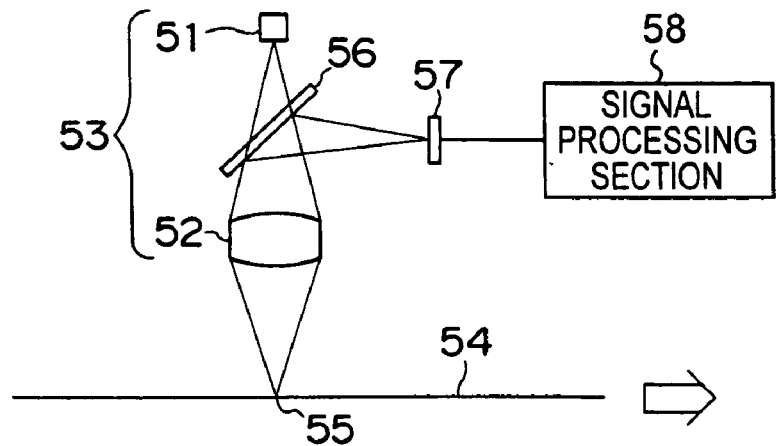
FIG. 10 is a schematic diagram showing an optical system in an optical object identification apparatus different from that in FIG. 1.

FIG. 10 is a schematic diagram showing optical systems in an optical object identification apparatus different from that in FIG. 1. The optical object identification apparatus in the present embodiment has a light emitting-side optical system 53 including a light emitting device (preferably a semiconductor laser) 51 and an objective and light receiving lens 52. By irradiating light emitted from the light emitting-side optical system 53 to a target object 54, a light spot 55 having a specified spot diameter (not more than 50 $\mu$m) is formed on the target object 54 moving in an arrow direction, and after reflected light from the light spot 55 is condensed by the objective and light receiving lens 52, the light is brought incident to the light receiving device 57 with its optical axis bent 90 degrees by a beam splitter 56. More specifically, the light receiving-side optical system is composed of the objective and light receiving lens 52, the beam splitter 56 and the light receiving device 57, and shares the objective and light receiving lens 52 with the light emitting-side optical system 53.

A signal processing section 58 executes signal processing of a specified length section of the output signal having an output waveform corresponding to the surface state (surface projections and depressions) of the target object 54 outputted from the light receiving device 57. Therefore, based on this processing result, the type of the light spot 55 can be detected.

It is noted that in the present embodiment as well, a light receiving-side optical system made up of the beam splitter 56 and the light receiving device 57 may be constituted similarly to the case shown in FIG. 2, FIG. 5 or FIG. 7 in the first embodiment so as to accomplish more definite identification of the type of the target object 54 with use of polarization.

Alternatively, without use of polarization, the signal processing section 58 may execute a combination of two or more of the aforementioned signal processing methods consisting of the "mean value calculating method", "mean amplitude value calculating method", "mean-amplitude/mean value calculating method", "frequency distribution calculating method", "power spectral area ratio calculating method", and "filter passing method".

Alternatively, without use of polarization, the signal processing section 58 may execute at least one of the aforementioned signal processing methods on a specified length section (specified length of time) of the output signal a plurality of times, and calculate a mean value of the thus obtained processing results.

Meantime, an optical axis of the light emitting-side optical system 53 and an optical axis of the light receiving-side optical system (specifically, of the objective and light receiving lens 52) in the present embodiment are vertical to the face of the target object 54. Therefore, even if a distance between the optical object identification apparatus and the target object 54 is fluctuated due to vibration or the like of the target object 54, the light spot on the target object 54 still exists on the optical axis of the light receiving-side optical system 52. Therefore, it becomes possible to provide an optical object identification apparatus that is less susceptible to fluctuation of the distance to the target object 54.

(Third Embodiment)

Figure 11:
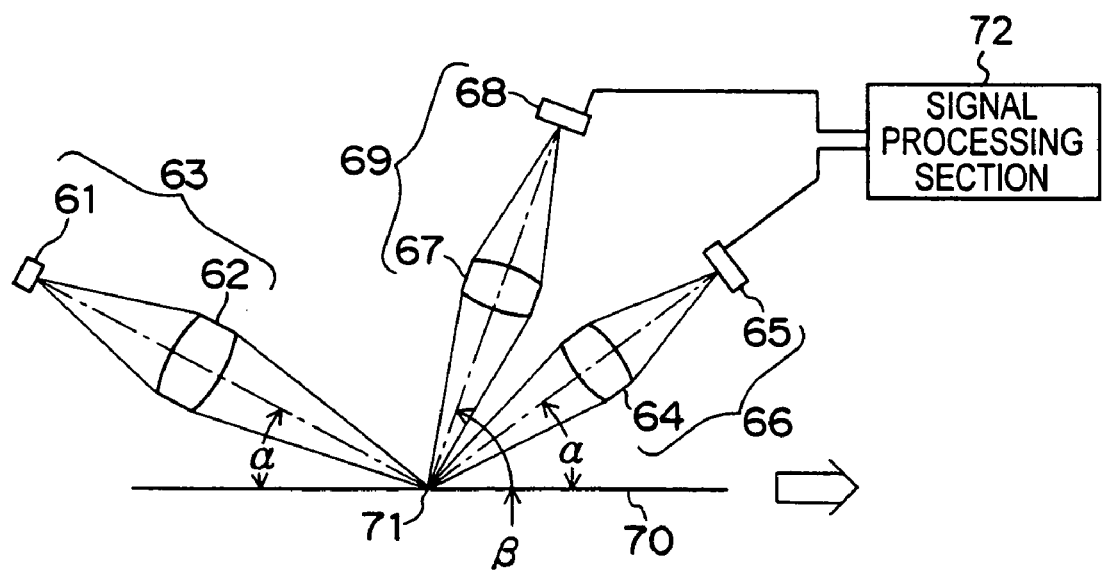
FIG. 11 is a schematic diagram showing optical systems in an optical object identification apparatus different from those in FIG. 1 and FIG. 10.

FIG. 11 is a schematic diagram showing optical systems in an optical object identification apparatus of the present embodiment. The optical object identification apparatus in the present embodiment has one light emitting-side optical system 63 including a light emitting device (preferably a semiconductor laser) 61 and an objective lens 62, and two light receiving-side optical systems composed of a first light receiving-side optical system 66 including a light receiving lens 64 and a light receiving device 65, and a second light receiving-side optical system 69 including a light receiving lens 67 and a light receiving device 68. In this case, these two light receiving-side optical systems 66, 69 are disposed such that an angle $\alpha$ between an optical axis of one of these two light receiving-side optical systems 66, 69 (the first light receiving-side optical system 66 in the case of FIG. 11) and a target object 70 is equal to an angle $\alpha$ between an optical axis of the light emitting-side optical system 63 and the target object 70, while an angle $\beta$ between an optical axis of the other light receiving-side optical system (the second light receiving-side optical system 69 in the case of FIG. 11) and the target object 70 is larger than the angle $\alpha$.

Then, by irradiating light emitted from the light emitting-side optical system 63 to the target object 70, a light spot 71 having a specified spot diameter (not more than 50 $\mu$m) is formed on the target object 70 moving in an arrow direction, and while regularly reflected light from the light spot 71 is brought incident to the first light receiving-side optical system 66, diffuse-reflected light from the light spot 71 is brought incident to the second light receiving-side optical system 69. Thus, the regularly reflected light and the diffuse-reflected light from the target object 70 are received.

A signal processing section 72 executes signal processing of an output signal based on the regularly reflected light from the light receiving device 65 in the first light receiving-side optical system 66 and an output signal based on the diffuse-reflected light from the light receiving device 68 in the second light receiving-side optical system 69, respectively, by at least one of the aforementioned signal processing methods: the "mean value calculating method", "mean amplitude value calculating method", "mean-amplitude/mean value calculating method", "frequency distribution calculating method", "power spectral area ratio calculating method", and "filter passing method". Then, a ratio between the processing result for the regularly reflected light and the processing result for the diffuse-reflected light is calculated.

In the present embodiment, the processing result for the regularly reflected light and the processing result for the diffuse-reflected light are used, so that the type of the target object 70 can be identified more accurately than in the case of using only one processing result for the regularly reflected light.

It is noted that the signal processing executed by the signal processing section 72 in this embodiment is not limited to the calculation of the ratio between the processing result for the regularly reflected light and the processing result for the diffuse-reflected light. Therefore it is also acceptable to calculate a mean value of a plurality of processing results obtained by executing at least one of the aforementioned signal processing methods on a specified length section (specified length of time) of the output signal in each of the light receiving-side optical systems 66, 69 a plurality of times, and then calculate a ratio of these mean values for the light receiving-side optical systems 66, 69.

Alternatively, in the case where two light receiving-side optical systems 66, 69 are provided as with the present embodiment, only one light receiving-side optical system may be constituted like that shown in FIG. 2, FIG. 5, or FIG. 7 in the above described first embodiment, and at least one of the aforementioned signal processing methods may be executed on the output signals from the light receiving devices of both light receiving-side optical systems by the signal processing section 72, and a ratio of the thus obtained processing results may be calculated.

Alternatively, both of the two light receiving-side optical systems 66, 69 may be constituted as shown in FIG. 2, FIG. 5 or FIG. 7 of the above-described first embodiment, and at least one of the aforementioned signal processing methods may be executed on a detection signal based on light that passed a polarizing plate (polarization device) and a detection signal based on light that does not pass the polarizing plate in the respective light receiving-side optical systems. Then, a ratio between the processing results based on the light that passed the polarizing plate (device) in the respective light receiving-side optical systems, or a ratio between the processing results based on the light that does not pass the polarizing plate (polarization device) may be calculated.

(Fourth Embodiment)

Figure 12:
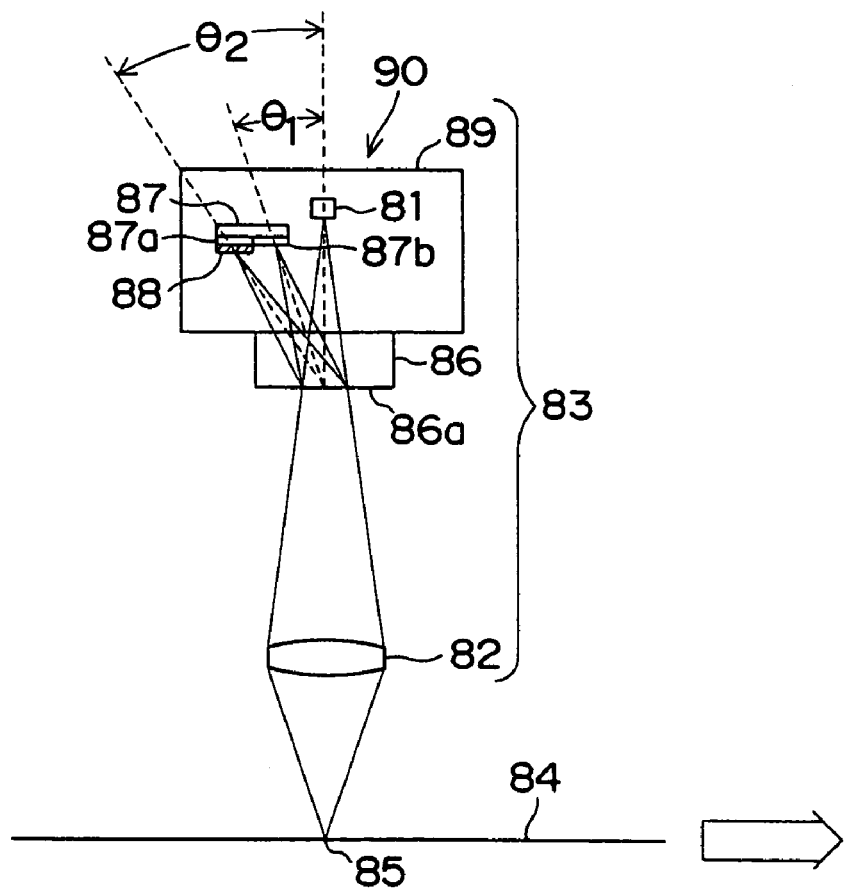
FIG. 12 is a schematic diagram showing an optical system in an optical object identification apparatus different from those in FIG. 1, FIG. 10 and FIG. 11.

FIG. 12 is a schematic diagram showing optical systems in an optical object identification apparatus in the present embodiment. The optical object identification apparatus in this embodiment is a modification of the optical object identification apparatus in the above-described second embodiment.

The optical object identification apparatus has a light emitting-side optical system 83 including a light emitting device (preferably a semiconductor laser) 81 and an objective and light receiving lens 82. By irradiating light emitted from the light emitting-side optical system 83 to a target object 84, a light spot 85 having a given spot diameter (not more than 50 μm) is formed on the target object 84 moving in an arrow direction, and reflected light from the light spot 85 is collected by the objective and light receiving lens 82 and is brought incident upon a hologram 86.

Figure 13:
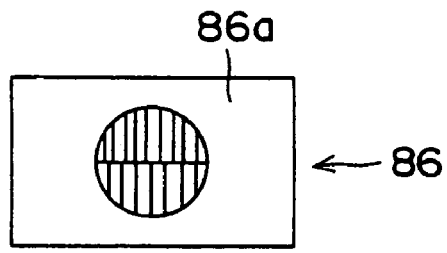
FIG. 13 is an explanatory view showing an interference pattern of a hologram in FIG. 12.

The hologram 86, which has a characteristic that the intensity of zero-order diffraction light is considerably smaller than the intensity of ± first-order and +second-order diffraction light, makes diffracted light enter a light receiving chip 87. In this case, as shown in FIG. 13, an interference pattern of the hologram 86 is formed in each of two regions provided by dividing a circle put on a surface 86a into halves, and pattern pitches in each region are different from each other. Therefore, two diffraction angles θ1 and θ2 are generated, and light is brought incident upon two light receiving faces 87a, 87b of the single light receiving chip 87. Here, a polarization device 88 is formed on one light receiving face 87a.

Consequently, at least one of the aforementioned signal processing methods of the "mean value calculating method", "mean amplitude value calculating method", "mean-amplitude/mean value calculating method", "frequency distribution calculating method", "power spectral area ratio calculating method", and "filter passing method" is executed on a detection signal from the light receiving face 87a based on light that passed the polarization device 88 and a detection signal from the light receiving face 87b based on light that does not pass the polarization device 88, respectively, by a signal processing section (unshown), and a ratio between these processing results is calculated. This implements more accurate identification of the type of the target object 84.

The light emitting device 81, the light receiving chip 87 and the polarization device 88 are formed in one package 89, and the hologram 86 is mounted on the package 89 to constitute an integrated unit 90. This means that the light emitting-side optical system 83 in the present embodiment also constitutes the light receiving-side optical system. According to the present embodiment, therefore, when the optical object identification apparatus is placed on a copying apparatus and the like, it is not necessary to pay attention to adjustment of the placement angles of the light emitting device and the light receiving device if the integrated unit 90 and the objective and light receiving lens 82 are unitized in advance, which makes it easy to mount the optical object identification apparatus on a copying apparatus and the like. In addition, it becomes possible to increase light receiving accuracy and also increase identification accuracy of the type of the target object 84.

(Fifth Embodiment)

This embodiment relates to printing apparatuses such as printers and copying machines incorporating the optical object identification apparatus according to any one of the above-described embodiments.

Figure 14:
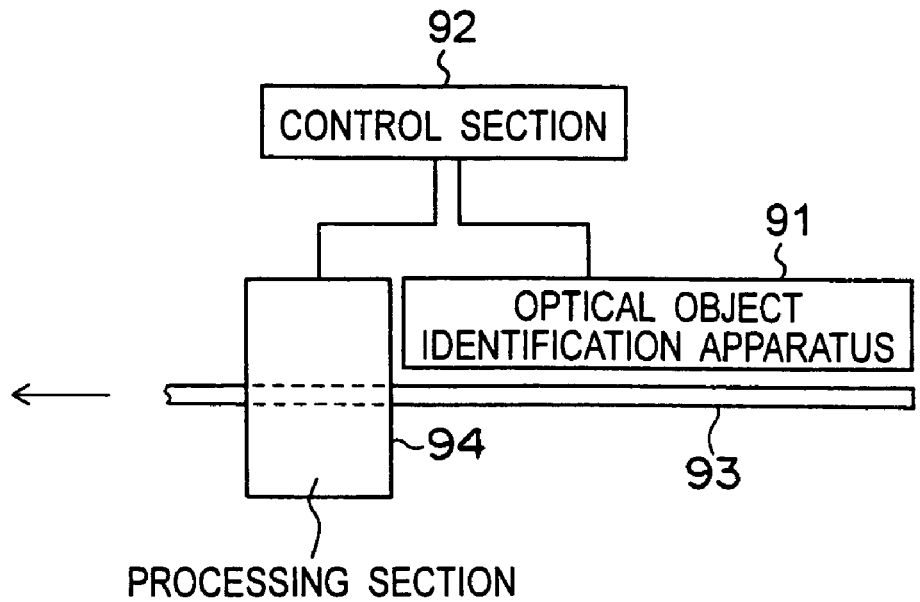
FIG. 14 is a view showing the concept of a printing apparatus of the present invention.
Figure 15:
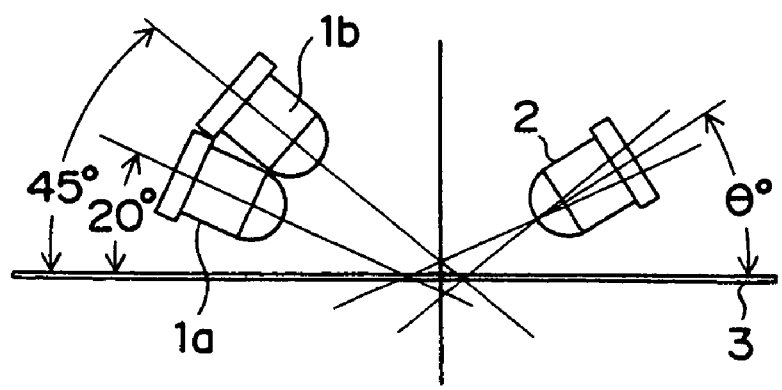
FIG. 15 is an explanatory view showing a paper type detection device as one example of conventional object identification apparatuses.
Figure 16:
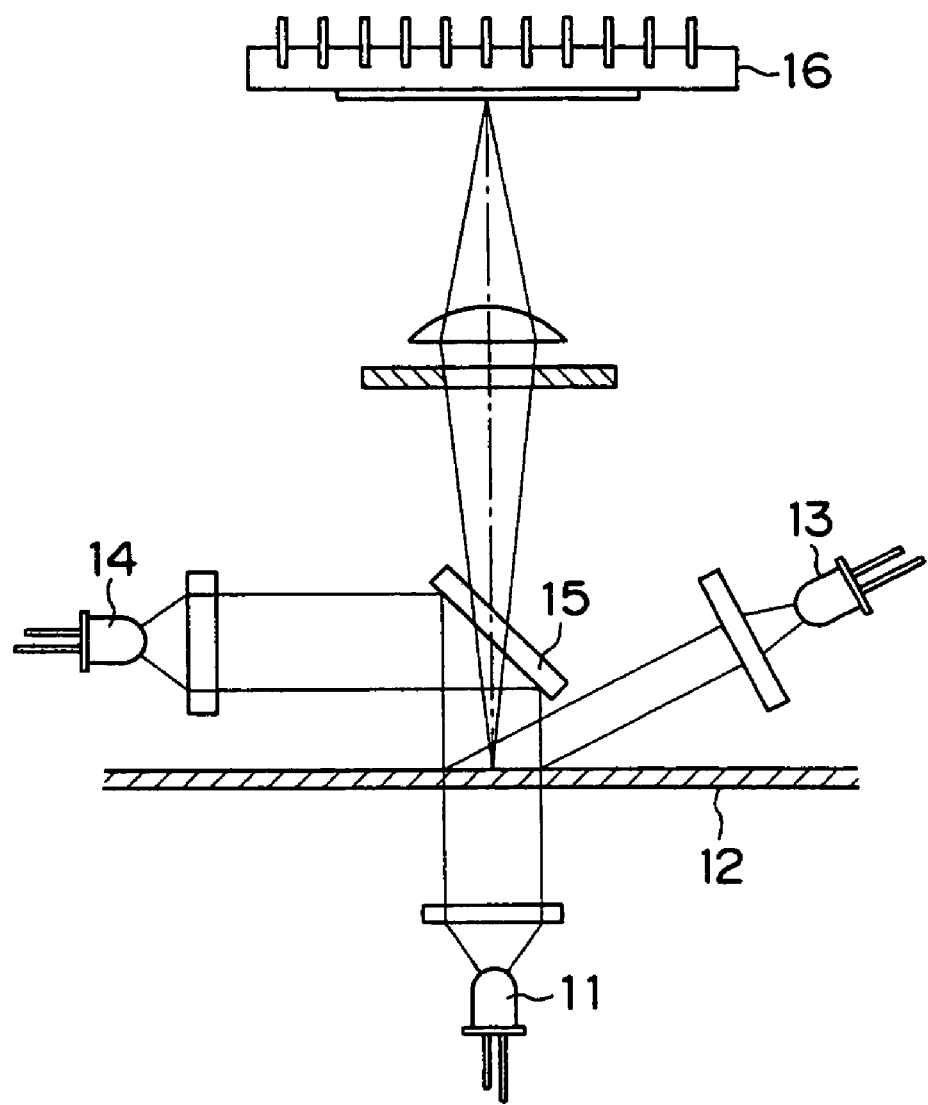
FIG. 16 is an explanatory view showing a recording media identification device as one example of conventional object identification apparatuses.

FIG. 14 shows the concept of target object type identification and control in a printing apparatus according to the present embodiment. An optical object identification apparatus 91 has the constitution of any one of the optical object identification apparatuses described in the first embodiment to the fourth embodiment. Under the control by a control section 92, signal processing of an output signal from a light receiving device based on reflected light from a moving target object 93 is executed as described above, and a signal representing the processing result is sent from the optical object identification apparatus 91 to the control section 92.

Eventually, the control section 92 identifies the type of the target object 93 based on the signal sent from the optical object identification apparatus 91, and sends to a processing section 94 a control signal for executing a processing corresponding to the identification result. The processing section 94 then executes the processing corresponding to the control signal. In the case where the printing apparatus is an ink-jet printer for example, the type of a paper sheet, or target object 93, is identified by the control section 92, and printing conditions such as amounts of inks suitable for the identified type of the paper sheet are optimized by the processing section 94.

During the operation, based on an output signal having a waveform corresponding to the surface state (surface projections and depressions) of the target object 93, the optical object identification apparatus 91 executes signal processing of different detection signals based on rays of light that have passed and that have not passed the polarization device, signal processing by different signal processing methods, signal processing of different detection signals based on regularly reflected and diffuse-reflected rays of light, or signal processing of different sections of the detection signals. Therefore, the type of the target object 93 can be identified more accurately than the case in which the type of the target object is identified only from the amount of reflected light from the target object, as described in the first embodiment to the fourth embodiment.

Thus, the printing apparatus incorporating the optical object identification apparatus 91 allows optimization of the printing conditions and further improvement of the printing quality.

It is noted that if the processing section 94 is constituted so as to classify the target object 93 based on the control signal from the control section 92, then it becomes possible to constitute an object classification apparatus that identifies and classifies the target object 93 from the optical object identification apparatus 91, the control section 92 and the processing section 94.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. An optical object identification apparatus, comprising:
   at least one light emitting-side optical system that includes a light emitting device and an objective lens, and that irradiates light from the light emitting device to a moving target object and forms a light spot on the target object;
   at least one light receiving-side optical system that includes a light receiving lens and a light receiving device, and that outputs an output signal having a waveform corresponding to surface projections and depressions of the target object when reflected light from the light spot enters the light receiving device;
   a signal processing section that executes signal processing of the out put signal outputted from the light receiving-side optical system;
   wherein the light emitted from the light emitting device is polarized light whose direction of polarization is vertical or parallel to a plane of incidence;
   wherein the light receiving-side optical system has two light receiving devices, the optical object identification apparatus further comprising:
   a beam splitter provided in the light receiving-side optical system for letting the reflected light from the light spot come incident to each of the two light receiving devices; and
   polarization means disposed immediately before one of the light receiving devices in the light receiving-side optical system for passing polarized light having a direction of polarization that is orthogonal to the direction of polarization of the light emitted from the light emitting device.

2. An optical object identification apparatus, comprising:
   at least one light emitting-side optical system includes a light emitting device and an objective lens, and that irradiates light from the light emitting device to a moving target object and forms a light spot on the target object;
   at least one light receiving-side optical system that includes a light receiving lens and a light receiving device, and that outputs an output signal having a waveform corresponding to surface projections and depressions of the target object when reflected light from the light spot enters the light receiving device;
   a signal processing section that executes signal processing of the output signal outputted from the light receiving-side optical system;
   wherein the light emitted from the light emitting device is polarized light whose direction of polarization is vertical or parallel to a plane of incidence;
   two light receiving regions provided in the light receiving device;
   a diffraction grating provided in the light receiving-side system and designed such that intensity of zero-order diffraction light is sufficiently smaller than intensity of ± first-order diffraction light; and
   polarization means disposed immediately before one of the light receiving regions in the light receiving device for passing polarized light having a direction of polarization that is orthogonal to the direction of polarization of the light emitted from the light emitting device, wherein
   the ± first-order diffraction light from the diffraction grating enters the two right receiving regions.

3. An optical object identification apparatus, comprising:
   at least one light emitting-side optical system includes a light emitting device and an objective lens, and that irradiates light from the light emitting device to a moving target object and forms a light spot on the target object;
   at least one light receiving-side optical system that includes a light receiving lens and a light receiving device, and that outputs an output signal having a waveform corresponding to surface projections and depressions of the target object when reflected light from the light spot enters the light receiving device;
   a signal processing section that executes signal processing of the output signal outputted from the light receiving-side optical system;
   wherein the light emitted from the light emitting device is polarized light whose direction of polarization is vertical or parallel to a plane of incidence;
   wherein the light receiving device in the light receiving-side optical system is disposed in a position closer to the light receiving lens than a location of an image of the light spot formed by the light receiving lens is,
   polarization means disposed immediately before a half region of a light receiving face in the light receiving device is provided for passing polarized light having direction of polarization that is orthogonal to the direction of polarization of the light emitted from the light emitting device, and
   an image of the light spot formed on the light receiving face of the light receiving device by the light receiving lens is formed in a boundary between a region of the light receiving face on which the polarization means is disposed and region of the light receiving face on which the polarization means in not disposed.

4. The optical object identification apparatus as claimed in claim 1, wherein the polarization means comprises a polarization device formed on the one light receiving device.

5. The optical object identification apparatus as claimed in claim 2, wherein the polarization means comprises a polarization device formed on the light receiving region.

6. The optical object identification apparatus as claimed in claim 3, wherein the polarization means is a polarization device formed on the light receiving device.

7. An optical object identification apparatus, comprising:
   at least one light emitting-side optical system includes a light emitting device and an objective lens, and that irradiates light from the light emitting device to a moving target object and forms a light spot on the target object;
   at least one light receiving-side optical system that includes a light receiving lens and a light receiving device, and that outputs an output signal having a waveform corresponding to surface projections and depressions of the target object when reflected light from the light spot enters the light receiving device;
   a signal processing section that executes signal processing of the output signal outputted from the light receiving-side optical system;
   wherein the signal processing section executes signal processing on a section of specifies length of time in the output signal by at least one signal processing means selected from the group consisting of:
      a mean value calculating means for calculating a mean value of output values;
      a mean amplitude value calculating means for obtaining differences between each of the output values and the mean value and doubling a mean value of absolute values of these differences;

a mean-amplitude/mean value calculating means for calculating the mean amplitude value divided by the mean value;

a frequency distribution calculating means for obtaining frequency distribution of the output values with a maximum value being set to 1;

a power spectral area ration calculating means for obtaining spectral distribution by applying Fourier transform and obtaining an area ratio between different distribution ranges in the spectral distribution; and a filter passing means for calculating at least one of the mean value, the mean amplitude value, and the mean amplitude divided by the mean value after passing the output signal through a filter circuit.

8. The optical object identification apparatus as claimed in claim 7, wherein the signal processing section executes signal processing by at least two of the mean value calculating means, the mean amplitude value calculating means, the mean-amplitude/mean value calculating means, the frequency distribution calculating means, the power spectral area ratio calculating means, and the filter passing means, and calculates a ratio between processing results obtained by these two signal processing means.

9. An optical object identification apparatus, comprising:

at least one light emitting-side optical system includes a light emitting device and an objective lens, and that irradiates light from the light emitting device to a moving target object and forms a light spot on the target object;

at least one light receiving-side optical system that includes a light receiving lens and a light receiving device, and that outputs an output signal having a waveform corresponding to surface projections and depressions of the target object when reflected light from the light spot enters the light receiving device;

a signal processing section that executes signal processing of the output signal outputted from the light receiving-side optical system;

one light emitting-side optical system; and two light receiving-side optical system, wherein an angle between an optical axis of one of the two light receiving-side optical systems and a light spot formation face of the target object is equal to an angle between an optical axis of the light emitting-side optical system and the light spot formation face of the target object;

wherein the signal processing section executes signal processing on respective output signals from the two light receiving-side optical systems by at least any one of:

a mean value calculating means for calculating a mean value of output values;

a mean amplitude value calculating means for obtaining differences between each of the output values and the mean value and doubling a mean value of absolute values of these differences;

a mean-amplitude/mean value calculating means for calculating the mean amplitude value divided by the mean value;

a frequency distribution calculating means for obtaining frequency distribution of the output values with a maximum value being set to 1;

a power spectral area ratio calculating means for obtaining spectral distribution by applying Fourier transform and obtaining an area ratio between different distribution ranges in the spectral distribution; and a filter passing means for calculating at least one of the mean value, the mean amplitude value, and the mean amplitude divided by the mean value after passing the output signal through a filter circuit, and wherein the signal processing section calculates a ratio between processing results for these two light receiving-side optical systems.

10. The optical object identification apparatus as claimed in claim 1, wherein the signal processing section executes signal processing on two types of output signals that are respectively based on light that has passed the polarization means and light that has not passed the polarization means, by at least any one of:

a mean value calculating means for calculating a mean value of output values;

a mean amplitude value calculating means for obtaining differences between each of the output values and the mean value and doubling a mean value of absolute values of these differences;

a mean-amplitude/mean value calculating means for calculating the mean amplitude value divided by the mean value;

a frequency distribution calculating means for obtaining frequency distribution of the output values with a maximum value being set to 1;

a power spectral area ratio calculating means for obtaining spectral distribution by applying Fourier transform and obtaining an area ratio between different distribution ranges in the spectral distribution; and a filter passing means for calculating at least one of the mean value, the mean amplitude value, and the mean amplitude divided by the mean value after passing the output signal through a filter circuit, and wherein the signal processing section calculates a ratio between processing results of these two types of output signals.

11. The optical object identification apparatus as claimed in claim 2, wherein the signal processing section executes signal processing on two types of output signals that are respectively based on light that has passed the polarization means and light that has not passed the polarization means, by at least any one of:

a mean value calculating means for calculating a mean value of output values;

a mean amplitude value calculating means for obtaining differences between each of the output values and the mean value and doubling a mean value of absolute values of these differences;

a mean-amplitude/mean value calculating means for calculating the mean amplitude value divided by the mean value;

a frequency distribution calculating means for obtaining frequency distribution of the output values with a maximum value being set to 1;

a power spectral area ratio calculating means for obtaining spectral distribution by applying Fourier transform and obtaining an area ratio between different distribution ranges in the spectral distribution; and a filter passing means for calculating at least one of the mean value, the mean amplitude value, and the mean amplitude divided by the mean value after passing the output signal through a filter circuit, and wherein the signal processing section calculates a ratio between processing results of these two types of output signals.

12. The optical object identification apparatus as claimed in claim 3, wherein the signal processing section executes signal processing on two types output signals that are respectively based on light that has passed the polarization means ad light that has not passed the polarization means, by at least any one of:
- a mean value calculating means for calculating a mean value of output values;
- a mean amplitude value calculating means for obtaining differences between each of the output values and the mean value and doubling a mean value of absolute values of these differences;
- a mean-amplitude/mean value calculating means for calculating the mean amplitude value divided by the mean value;
- a frequency distribution calculating means for obtaining frequency distribution of the output values with a maximum value being set to 1;
- a power spectral area ratio calculating means for obtaining spectral distribution by applying Fourier transform and obtaining an area ratio between different distribution ranges in the spectral distribution; and
- a filter passing means for calculating at least one of the mean value, the mean amplitude value, and the mean amplitude divided by the mean value after passing the output signal through a filter circuit,
- and wherein the signal processing section calculates a ratio between processing results of these two types of output signals.

13. The optical object identification apparatus as claimed in claim 4, wherein the signal processing section executes signal processing on two types of output signals that are respectively based on light that has passed the polarization means and light that has not passed the polarization means, by at least any one of:
- a mean value calculating means for calculating a mean value of output values;
- a mean amplitude value calculating means for obtaining differences between each of the output values and the mean value and doubling a mean value of absolute values of these differences;
- a mean-amplitude/mean value calculating means for calculating the mean amplitude value divided by the mean value;
- a frequency distribution calculating means for obtaining frequency distribution of the output values with a maximum value being set to 1;
- a power spectral area ratio calculating means for obtaining spectral distribution by applying Fourier transform and obtaining an area ratio between different distribution ranges in the spectral distribution; and
- a filter passing means for calculating at least one of the mean value, the mean amplitude value, and the mean amplitude divided by the mean value after passing the output signal through a filter circuit,
- and wherein the signal processing section calculates a ratio between processing results of these two types of output signals.

14. The optical object identification apparatus as claimed in claim 5, wherein the signal processing section executes signal processing on two types of output signals that are respectively based on light that has passed the polarization means and light that has not passed the polarization means, by at least any one of:
- a mean value calculating means for calculating a mean value of output values;
- a mean amplitude value calculating means for obtaining differences between each of the output values and the mean value and doubling a mean value of absolute values of these differences;
- a mean-amplitude/mean value calculating means for calculating the mean amplitude value divided by the mean value;
- a frequency distribution calculating means for obtaining frequency distribution of the output values with a maximum value being set to 1;
- a power spectral area ratio calculating means for obtaining spectral distribution by applying Fourier transform and obtaining an area ratio between different distribution ranges in the spectral distribution; and
- a filter passing means for calculating at least one of the mean value, the mean amplitude value, and the mean amplitude divided by the mean value after passing the output signal through a filter circuit,
- and wherein the signal processing section calculates a ratio between processing results of these two types of output signals.

15. The optical object identification apparatus as claimed in claim 6, wherein the signal processing section executes signal processing on two types of output signals that are respectively based on light that has passed the polarization means and light that has not passed the polarization means, by at least any one of:
- a mean value calculating means for calculating a mean value of output values;
- a mean amplitude value calculating means for obtaining differences between each of the output values and the mean value and doubling a mean value of absolute values of these differences;
- a mean-amplitude/mean value calculating means for calculating the mean amplitude value divided by the mean value;
- a frequency distribution calculating means for obtaining frequency distribution of the output values with a maximum value being set to 1;
- a power spectral area ratio calculating means for obtaining spectral distribution by applying Fourier transform and obtaining an area ratio between different distribution ranges in the spectral distribution; and
- a filter passing means for calculating at least one of the mean value, the mean amplitude value, and the mean amplitude divided by the mean value after passing the output signal through a filter circuit,
- and wherein the signal processing section calculates a ratio between processing results of these two types of output signals.

16. The optical object identification apparatus as claimed in claim 1, comprising
another light receiving-side optical system also having the polarization means, wherein
the signal processing section executes signal processing on two types of output signals that are respectively based on light that has passed the polarization means and light that has not passed the polarization means, for each of the two light receiving-side optical system, by at least any one of:
- a mean value calculating means for calculating a mean value of output values;
- a mean amplitude value calculating means for obtaining differences between each of the output values and the mean value and doubling a mean value of absolute values of these differences;

a mean-amplitude/mean value calculating means for calculating the mean amplitude value divided by the mean value;

a frequency distribution calculating means for obtaining frequency distribution of the output values with a maximum value being set to 1;

a power spectral area ratio calculating means for obtaining spectral distribution by applying Fourier transform and obtaining an area ratio between different distribution ranges in the spectral distribution; and a filter passing means for calculating at least one of the mean value, the mean amplitude value, and the mean amplitude divided by the mean value after passing the output signal through a filter circuit, and wherein the signal processing section calculates a ratio between processing results of the output signals of the two light receiving-side optical systems that have passed the polarization means, and a ratio between processing results of the output signals of the two light receiving-side optical systems that have not passed the polarization means.

17. The optical object identification apparatus as claimed in claim 2, comprising another light receiving-side optical system also having the polarization means, wherein the signal processing section executes signal processing on two types of output signals that are respectively based on light that has passed the polarization means and light that has not passed the polarization means, for each of the two light receiving-side optical systems, by at least any one of:

a mean value calculating means for calculating a mean value of output values;

a mean amplitude value calculating means for obtaining differences between each of the output values and the mean value and doubling a mean value of absolute values of these differences;

a mean-amplitude/mean value calculating means for calculating the mean amplitude value divided by the mean value;

a frequency distribution calculating means for obtaining frequency distribution of the output values with a maximum value being set to 1;

a power spectral area ratio calculating means for obtaining spectral distribution by applying Fourier transform and obtaining an area ratio between different distribution ranges in the spectral distribution; and a filter passing means for calculating at least one of the mean value, the mean amplitude value, and the mean amplitude divided by the mean value after passing the output signal through a filter circuit, and wherein the signal processing section calculates a ratio between processing results of the output signals of the two light receiving-side optical systems that have passed the polarization means, and a ratio between processing results of the output signals of the two light receiving-side optical systems that have not passed the polarization means.

18. The optical object identification apparatus as claimed in claim 3, comprising another light receiving-side optical systems also having the polarization means, wherein the signal processing section executes signal processing on two types of output signals that are respectively based on light that has passed the polarization means and light that has not passed the polarization means, for each of the two light receiving-side optical systems, by at least any one of:

a mean value calculating means for calculating a mean value of output values;

a mean amplitude value calculating means for obtaining differences between each of the output values and the mean value and doubling a mean value of absolute values of these differences;

a mean-amplitude/mean value calculating means for calculating the mean amplitude value divided by the mean value;

a frequency distribution calculating means for obtaining frequency distribution of the output values with a maximum value being set to 1;

a power spectral area ratio calculating means for obtaining spectral distribution by applying Fourier transform and obtaining an area ratio between different distribution ranges in the spectral distribution; and a filter passing means for calculating at least one of the mean value, the mean amplitude value, and the mean amplitude divided by the mean value after passing the output signal through a filter circuit, and wherein the signal processing section calculates a ratio between processing results of the output signals of the two light receiving-side optical systems that have passed the polarization means, and a ratio between processing results of the output signals of the two light receiving-side optical systems that have not passed the polarization means.

19. The optical object identification apparatus as claimed in claim 4, comprising another light receiving-side system also have the polarization means, wherein the signal processing section executes signal processing on two types of output signals that are respectively based on light that has passed the polarization means and light that has not passed the polarization means, for each of the two light receiving-side optical systems, by at least any one of:

a mean value calculating means for calculating a mean value of output values;

a mean amplitude value calculating means for obtaining differences between each of the output values and the mean value and doubling a mean value of absolute values of these differences;

a mean-amplitude/mean value calculating means for calculating the mean amplitude value divided by the mean value;

a frequency distribution calculating means for obtaining frequency distribution of the output values with a maximum value being set to 1;

a power spectral area ratio calculating means for obtaining spectral distribution by applying Fourier transform and obtaining an area ratio between different distribution ranges in the spectral distribution; and a filter passing means for calculating at least one of the mean value, the mean amplitude value, and the mean amplitude divided by the mean value after passing the output signal through a filter circuit, and the signal processing section calculates a ratio between processing results of the output signals of the two light receiving-side optical systems that have passed the polarization means, and a ratio between processing results of the output signals of the two light receiving-side optical systems that have not passed the polarization means.

20. The optical object identification apparatus as claimed in claim 5, comprising another light receiving-side optical system also having the polarization means, wherein the signal processing section executes signal processing on two types of output signals that are respectively based on light that has passed the polarization means and light that has not passed the polarization means, for each of the two light receiving-side optical systems, by at least any one of:

a mean value calculating means for calculating a mean value of output values;

a mean amplitude value calculating means for obtaining differences between each of the output values and the mean value and doubling a mean value of absolute values of these differences;

a mean-amplitude/mean value calculating means for calculating the mean amplitude value divided by the mean value;

a frequency distribution calculating means for obtaining frequency distribution of the output values with a maximum value being set to 1;

a power spectral area ratio calculating means for obtaining spectral distribution by applying Fourier transform and obtaining an area ratio between different distribution ranges in the spectral distribution; and a filter passing means for calculating at least one of the mean value, the mean amplitude value, and the mean amplitude divided by the mean value after passing the output signal through a filter circuit, and wherein the signal processing section calculates a ratio between processing results of the output signals of the two light receiving-side optical systems that have passed the polarization means, and a ratio between processing results of the output signals of the two light receiving-side optical systems that have not passed the polarization means.

21. The optical object identification apparatus as claimed in claim 6, comprising another light receiving-side optical system also having the polarization means, wherein the signal processing section executes signal processing on two types of output signals that are respectively based on light that has passed the polarization means and light that has not passed the polarization means, for each of the two light receiving-side optical systems, by at least any one of:

a mean value calculating means for calculating a mean value of output values;

a mean amplitude value calculating means for obtaining differences between each of the output values and the mean value and doubling a mean value of absolute values of these differences;

a mean-amplitude/mean value calculating means for calculating the mean amplitude value divided by the mean value;

a frequency distribution calculating means for obtaining frequency distribution of the output values with a maximum value being set to 1;

a power spectral area ratio calculating means for obtaining spectral distribution by applying Fourier transform and obtaining an area ratio between different distribution ranges in the spectral distribution; and a filter passing means for calculating at least one of the mean value, the mean amplitude value, and the mean amplitude divided by the mean value after passing the output signal through a filter circuit, and wherein the signal processing section calculates a ratio between processing results of the output signals of the two light receiving-side optical systems that have passed the polarization means, and a ratio between processing results of the output signals of the two light receiving-side optical systems that have not passed the polarization means.

22. An optical object identification apparatus, comprising:

at least one light emitting-side optical system that includes a light emitting device and an objective lens, and that irradiates light the light emitting device to a moving target object and forms a light spot on the target object;

at least one light receiving-side optical system that includes a light receiving lens and a light receiving device, and that outputs an output signal having a waveform corresponding to surface projections and depressions of the target object when reflected light from the light spot enters the light receiving device;

a signal processing section that executes signal processing of the output signal outputted from the light receiving-side optical system;

wherein the signal processing section executes signal processing on a plurality of different sections in the output signal obtained by movement of the target object, by at least any one of:

a mean value calculating means for calculating a mean value of output values;

a mean amplitude value calculating means for obtaining differences between each of the output values and the mean value and doubling a mean value of absolute values of these differences;

a mean-amplitude/mean value calculating means for calculating the mean amplitude value divided by the mean value;

a frequency distribution calculating means for obtaining frequency distribution of the output values with a maximum value being set to 1;

a power spectral area ratio calculating means for obtaining spectral distribution by applying Fourier transform and obtaining an area ratio between different distribution ranges in the spectral distribution; and a filter passing means for calculating at least one of the mean value, the mean amplitude value, and the mean amplitude divided by the mean value after passing the output signal through a filter circuit, and wherein the signal processing section calculates a mean value of processing results of the plurality of the sections.

23. A printing apparatus incorporating the optical object identification apparatus of claim 1.

24. An object classification apparatus incorporating the optical object identification apparatus of claim 1.

25. The apparatus of claim 1, wherein the target object is paper.

26. The apparatus of claim 2, wherein the target object is paper.

27. The apparatus of claim 3, wherein the target object is paper.

28. The apparatus of claim 7, wherein the target object is paper.

29. The apparatus of claim 9, wherein the target object is paper.

* * * * *